US00PP34988P2

(12) United States Plant Patent
Verschoor

(10) Patent No.: US PP34,988 P2
(45) Date of Patent: Feb. 14, 2023

(54) ***HELIOPSIS* PLANT NAMED 'LUNA ROJA'**

(50) Latin Name: ***Heliopsis helianthoides* var. *scabra***
Varietal Denomination: Luna Roja

(71) Applicant: Janus Verschoor, Haarlem (NL)

(72) Inventor: Janus Verschoor, Haarlem (NL)

( * ) Notice: Subject to any disclaimer, the term of this patent is extended or adjusted under 35 U.S.C. 154(b) by 0 days.

(21) Appl. No.: 17/893,959

(22) Filed: Aug. 23, 2022

(30) Foreign Application Priority Data

Dec. 3, 2021 (QZ) ..... PBR 20213171

(51) Int. Cl.
*A01H 5/02* (2018.01)
*A01H 6/14* (2018.01)

(52) U.S. Cl.
USPC ..... Plt./437
CPC ..... *A01H 6/14* (2018.05)

(58) Field of Classification Search
USPC ..... Plt./437
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Heliopsis* plant named 'Luna Roja' that is characterized by its dwarf plant size, its strong flowering stems, its foliage that is dark green-purple to green-black in color, its inflorescences with ray florets that are orange-red in color, and its blooming from midsummer to early autumn in The Netherlands.

2 Drawing Sheets

Botanical classification: *Heliopsis helianthoides* var. *scabra*.

Variety denomination: 'Luna Roja'.

CROSS REFERENCE TO A RELATED APPLICATION

This application claims foreign priority to European plant breeders' rights application filed on Dec. 3, 2021, application No. 2021/3171. The Applicant received the information for the Plant breeders' rights application directly from the Inventor.

BACKGROUND OF THE INVENTION

The present invention relates to a new and distinct cultivar of *Heliopsis* plant, botanically known as *Heliopsis helianthoides* var. *scabra* 'Luna Roja' and will be referred to hereinafter by its cultivar name, 'Luna Roja'.

The new cultivar was discovered as a chance seedling growing in a trial field by the Inventor in Haarlem, The Netherlands in 2018. The seedling arose from seed collected from open pollinated plants in the field that contained numerous unnamed and unpatented proprietary *Heliopsis* seedlings from the Inventor's breeding program. The seeds were pooled and parentage of 'Luna Roja' is therefore unknown.

Asexual propagation of the new cultivar was first accomplished by stem cuttings under the direction of the Inventor in summer of 2019 in Haarlem, The Netherlands. Asexual propagation by stem cuttings and tissue culture using meristematic tissue has shown that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Luna Roja' as a unique cultivar of *Heliopsis*.

1. 'Luna Roja' exhibits a dwarf plant size.
2. 'Luna Roja' exhibits strong flowering stems (that do not lodge).
3. 'Luna Roja' exhibits foliage that is dark green-purple to green-black in color.
4. 'Luna Roja' exhibits inflorescences with ray florets that are orange-red in color.
5. 'Luna Roja' exhibits blooms from midsummer to early autumn in The Netherlands.

'Luna Roja' can be compared to *Heliopsis* cultivars 'Bleeding Hearts' (not patented), 'Fire Twister' (U.S. Plant Pat. No. 25,524) and 'Tuscan Sun' (U.S. Plant Pat. No. 18,763). 'Bleeding Hearts' and 'Fire Twister' are both similar to 'Luna Roja' in inflorescence and foliage color. 'Bleeding Hearts' and 'Fire Twister' both differ from 'Luna Roja' in having a much taller plant height. 'Tuscan Sun' is similar to 'Luna Roja' in having a compact plant habit. 'Tuscan Sun' differs from 'Luna Roja' in having foliage that is green in color and inflorescences that are smaller in size and yellow in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales that fall within a one-year grace period prior to the filing date. Disclosures include website listings on websites by Growing Colors, Plantipp, Hayloft Plants, Vision Pictures, QVCUK, Baldur-Garten, Viridea, Globe Planter, Hortweek, Groupon, and Nursery Management.

BRIEF DESCRIPTION OF THE DRAWINGS

The accompanying color photographs illustrate the overall appearance and distinct characteristics of the new *Heliopsis*. The photographs were taken of a plant 12 months in age as field grown in Haarlem, The Netherlands and placed in a 15-cm container for the photographs in Haarlem, The Netherlands.

The photograph in FIG. 1 provides a side view of a plant of 'Luna Roja' in bloom.

Figure 1:
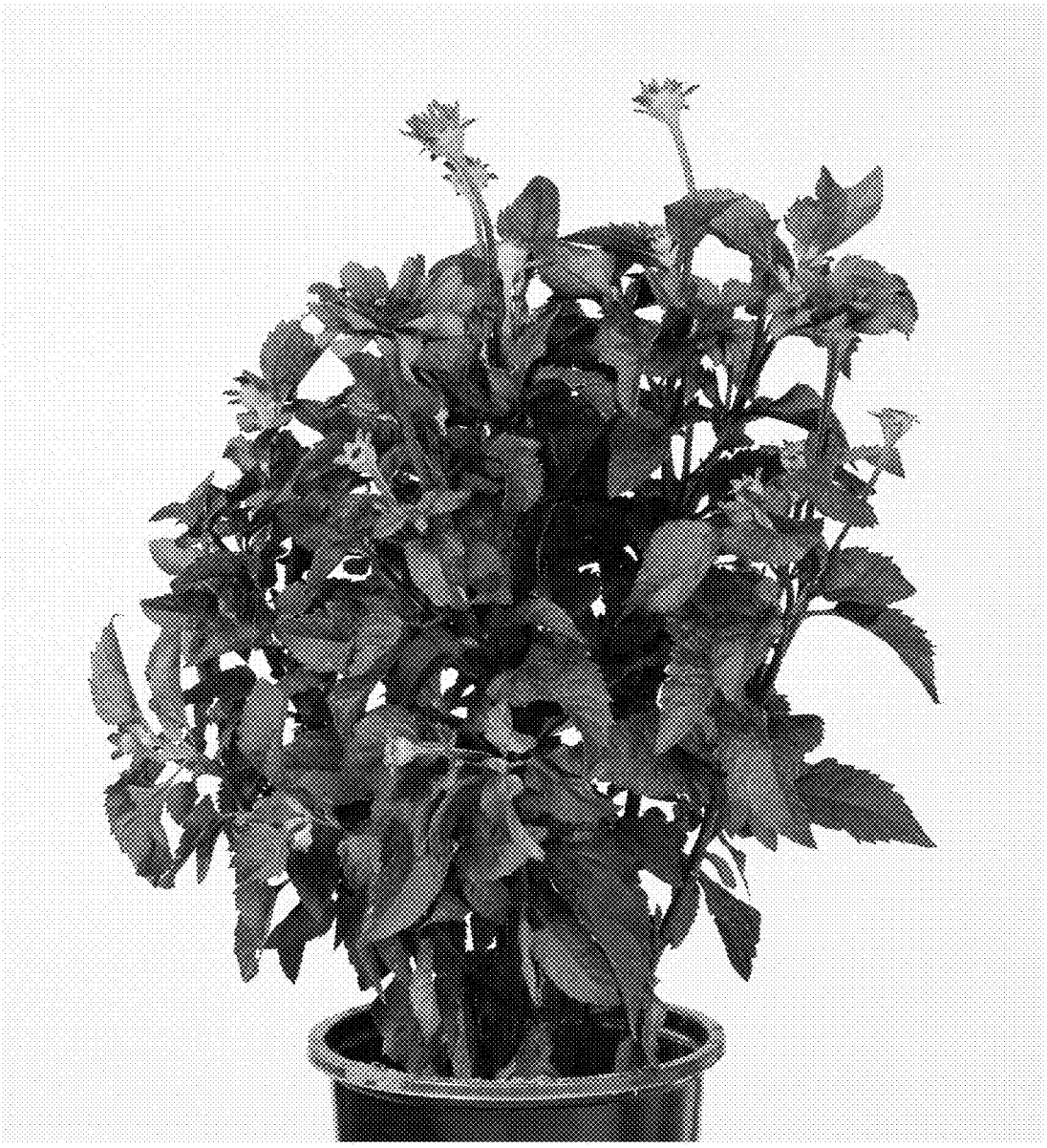
Figure 2:
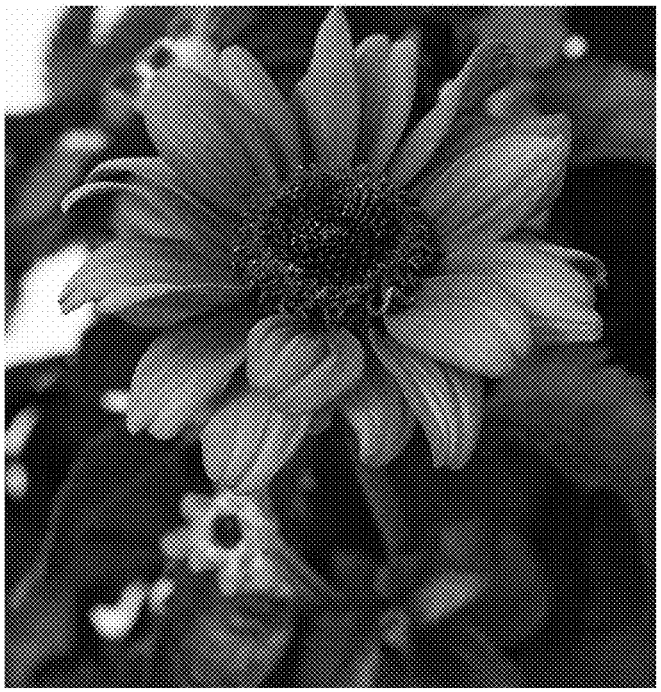

The photograph in FIG. 2 provides a close-up view of an inflorescence of 'Luna Roja'.

Figure 3:
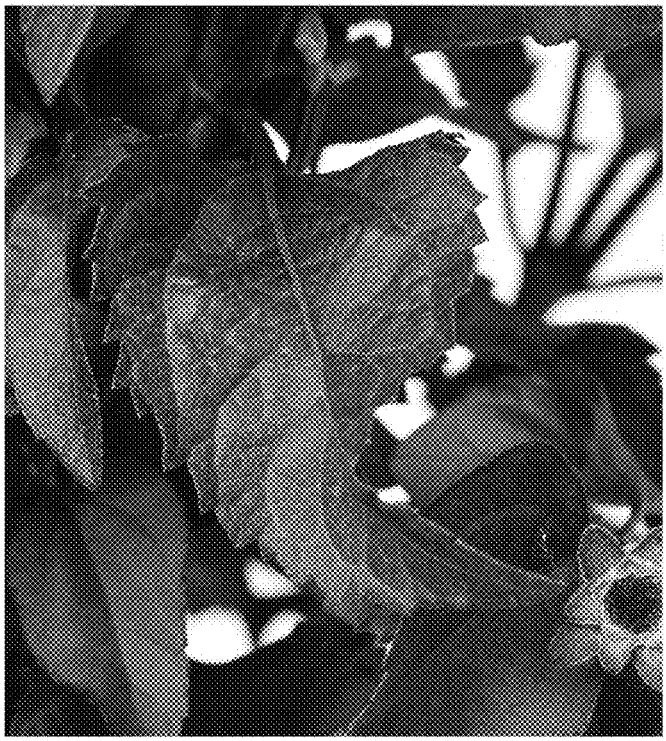

The photograph in FIG. 3 provides a close-up view of a leaf of 'Luna Roja'.

The colors in the photographs are as close as possible with the photographic and printing technology utilized and the color values cited in the detailed botanical description accurately describe the colors of the new *Heliopsis*.

DETAILED BOTANICAL DESCRIPTION

The following is a detailed description of plants 12 months in age as field grown in Haarlem, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—From midsummer to early autumn (July to October) in The Netherlands.

*Plant type*.—Herbaceous perennial.

*Plant habit*.—Dwarf, narrow, spreading-upright.

*Plant size*.—Average of 40 cm in height (soil level to top of foliar plane), 42.8 cm in height (soil level to top of floral plane), and 29 cm in spread.

*Hardiness*.—At least in U.S.D.A. Zones 4 to 9.

*Diseases and pests*.—No susceptibility or resistance to diseases or pests has been observed.

*Root description*.—Fibrous.

*Propagation*.—Stem cuttings and tissue culture.

*Root development*.—1 to 2 weeks for root initiation, a fully rooted young plant is produced in three to four weeks.

*Growth rate*.—Moderately vigorous.

Branch description:

*Branch shape*.—Rounded and slightly angled, 5-sided.

*Branch aspect*.—Main and vertical branches 20° from vertical.

*Branch strength*.—Moderately strong to strong.

*Branch color*.—Young stems; N186C, internodes 184A, mature stems; N186B, N186C and a blend of N186B and N186C.

*Branch surface*.—Young stems; moderately glossy, moderately pubescent, hairs 0.2 mm in length, 156D in color, mature stems; glabrous, moderately glossy.

*Branch size*.—Average of 8.3 cm in length, 3.5 mm in diameter.

*Internode length*.—Average of 3.3 cm.

*Branching*.—Freely branching, average of 6 main branches, 5 lateral branches per main branch.

Foliage description:

*Leaf division*.—Simple.

*Leaf shape*.—Deltoid, slightly to moderately axially twisted.

*Leaf base*.—Broadly truncate to shallowly broadly truncate.

*Leaf apex*.—Acute.

*Leaf margin*.—Serrate, coarsely undulate.

*Leaf venation*.—Pinnate, upper surface 200A, lower surface 187A.

*Leaf attachment*.—Petiolate.

*Leaf arrangement*.—Opposite.

*Leaf surface*.—Upper surface; slightly rugose, matte, lower surface; very slightly glossy, moderately rugose, both surfaces moderately covered with very short strigose hairs, an average of 0.3 mm in length, 156C to 156D in color.

*Leaf color*.—Young foliage upper surface; 147A, young foliage lower surface; N199A to N199B and 200C, mature upper surface; 147A and N189A, mature lower surface; 148A, tinged with a blend of N186C and 200A.

*Leaf size*.—Average of 6.9 cm in length and 5 cm in width.

*Petiole*.—Strong, an average of 1.5 cm in length and 2 mm in diameter, upper surface; matte, glabrous, N186C in color, lower surface; moderately glossy, 187A in color, sparsely covered with very short strigose hairs, 0.3 mm in length, too small to measure color.

Flower description:

*Inflorescence type*.—Rotate, terminal capitulum consisting of a receptacle, disc florets and ray florets.

*Lastingness of inflorescence*.—Average of 10 days, persistent.

*Fragrance*.—No fragrance.

*Quantity of inflorescences*.—2 per lateral stem, 72 inflorescences and buds per plant.

*Inflorescence buds*.—About 1.5 cm in length, 2.7 cm in diameter (including involucral bracts), 1.5 cm in diameter (excluding involucral bracts), flattened in shape, immature ray florets pointing upward (near vertical), color; immature ray florets a blend of N186C and 200B, immature disc florets a blend of N186C and 187A, immature involucral bracts N200A, base; N144D, surface is matte and moderately pubescent with very short hairs, average of 0.02 cm in length, too small to measure color.

*Inflorescence size*.—An average of 2.1 cm in height and 6.3 cm in diameter.

*Receptacle*.—Triangular, average of 6 mm in depth and 1 cm in diameter, disc diameter 2.1 cm, 150D in color.

*Peduncle*.—10.9 cm in length, 3 mm in diameter, strong, upright, straight on top of lateral branch, a blend of N186C and 200A, very slightly glossy, moderately covered with very short adpressed hairs, an average of 0.3 mm in length, 156C in color.

*Involucral bracts (phyllaries)*.—Rotate, average of 20, 2 rows, outer bracts; 1.2 cm in length, 3.5 mm in width, un-fused, oblong in shape, acute tip, broadly cuneate base, entire margins, color; upper surface N200A, lower surface a blend of 200B and N200A, surface is glossy, matte and moderately pubescent with very short hairs, average of 0.02 cm in length, too small to measure color, inner bracts; 7 mm in length, 3 mm in width, un-fused, broad ovate in shape, acute tip, broadly cuneate base, entire margins, color; upper surface 145B, base 145C, lower surface 145A, surface is glossy, matte and moderately pubescent with very short hairs, average of 0.02 cm in length, too small to measure color.

*Spine*.—Single bract present next to each individual disc floret, spirally placed on disc, one bract next to each individual disc floret, surface smooth, glabrous, and moderately glossy, 7 mm in length, 1 mm in diameter, narrow oblong in shape, obtuse apex, broad cuneate base, color; apex 176A, mid-section and base 145C.

Ray florets (carpellate):

*Number*.—Average of 21, 2 rows.

*Arrangement*.—Rotate.

*Appearance*.—Smooth, glabrous, moderately carinate, nearly horizontal.

*Shape*.—Elliptic.

*Aspect*.—Nearly horizontal, slightly upward in an average angle of 20° to horizontal.

*Size*.—Average of 2.7 cm in length and 1 cm in width.

*Ray floret apex*.—Shallowly praemorse.

*Ray floret base*.—Attenuate.

*Ray floret margins*.—Entire.

*Ray floret texture*.—Upper surface velvety and matte, lower surface moderately velvety and very slightly glossy.

*Ray floret color*.—When opening upper surface; 173A, lower half 183A, when opening lower surface; N186C, when fully open upper surface; N172A, veins N170A, fading to 21A, lower half 185A, lower half a blend of 185A and 187C, when fully open lower surface; 165B, fading to 164A and 165B.

Disc florets (perfect):

*Quantity*.—Average of 200.

*Shape*.—Tubular.

*Arrangement*.—Spirally placed on disc in 9 rows.

*Disc floret apex*.—Upper 12.5% free, acute, entire margins.

*Disc floret base*.—Lower 87.5% fused.

*Disc floret texture*.—Both surfaces glabrous, slightly glossy, non-rugose.

*Size*.—Average of 9 mm in length and 3 mm in width.

*Color*.—When opening upper and lower surface N186C, mid-section and base transparent 145C, when fully open upper and lower surface 183A, mid-section and base transparent N144B, both surfaces fading to 183A, mid-section and base transparent and 152D.

Reproductive organs:

*Presence*.—Disc florets are perfect, ray florets are carpellate.

*Gynoecium*.—Pistil; 1, per disc and ray floret, 9 mm in length, stigma; cleft, 3 mm in diameter, color 183A, style; 7 mm in length, 183A in color, ovary; 185C in color.

*Androecium*.—Stamens; 5 per disc floret, filaments; 1.5 mm in length and 151D in color, anthers; narrow oblong in shape, 2.5 mm in length, 0.5 mm in width and N199A in color, pollen; low in quantity and 14A in color.

*Fruit and seed*.—No fruits or seeds observed to date.

It is claimed:

1. A new and distinct cultivar of *Heliopsis* plant named 'Luna Roja' as herein illustrated and described.

* * * * *